United States Patent [19]

Hrstka et al.

[11] 4,060,626
[45] Nov. 29, 1977

[54] INDOLE-CARBOXYLIC CARBON COMPOUNDS AND PHARMACEUTICAL COMPOSITIONS CONTAINING THEM

[75] Inventors: Vladimir Hrstka, Mannheim-Neuostheim; Manfred Hübner, Ludwigshafen; Manfred Kuhr, Mannheim-Sandhofen; Felix Helmut Schmidt, Mannheim-Seckenheim; Walter Aumüller, Kelkheim-Munster, all of Germany

[73] Assignee: Boehringer Mannheim G.m.b.H., Mannheim, Germany

[21] Appl. No.: 683,110

[22] Filed: May 4, 1976

Related U.S. Application Data

[63] Continuation of Ser. No. 322,818, Jan. 11, 1973, abandoned.

[30] Foreign Application Priority Data

Jan. 26, 1972 Germany ............................ 2203542

[51] Int. Cl.² .................... A61K 31/40; C07D 209/18
[52] U.S. Cl. .................. 424/274; 260/326.13 R; 260/518 A; 260/518 R; 260/519; 260/515 R; 260/515 A; 560/21; 560/23; 560/20; 560/34
[58] Field of Search ................ 260/326.13 R; 424/274

[56] References Cited

U.S. PATENT DOCUMENTS

| | | | |
|---|---|---|---|
| 3,332,846 | 7/1967 | Gordon | 424/274 |
| 3,626,071 | 12/1971 | Kariya et al. | 424/274 |
| 3,780,062 | 12/1973 | Kaiser et al. | 424/274 |

FOREIGN PATENT DOCUMENTS

| | | | |
|---|---|---|---|
| 442,303 | 1/1968 | Switzerland | 260/326.13 R |

OTHER PUBLICATIONS

Janos et al., C.A. 71: 91282y (1969).
Blaikie et al., C.A. 18: 1294 (1924).
Andrisano et al., C.A. 52: 6312f–6314c (1958).
Pappalardo et al., C.A. 53: 20029h–20030h (1959).
Lallemand et al., Bull. Soc. Chim, France, 1970(11), pp. 4091, 4097 & 4098.
Ambekar et al., C.A. 67: 82031f (1967).
Julia et al., C.A. 74: 3458w (1971).
Pappalardo et al. (I), C.A. 53: 21876g (1959).
Harvey, C.A. 49: 14733f (1955).
Allen, C.A. 61: 1835g (1964).
C.A. 41: 3093c, 3093d.

*Primary Examiner*—Ethel G. Love
*Attorney, Agent, or Firm*—Burgess, Dinklage & Sprung

[57] ABSTRACT

Indole-carboxylic acid compounds of the formula:

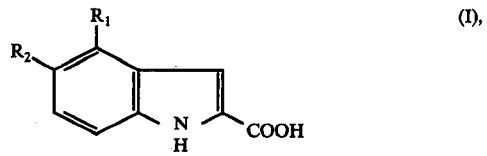

wherein
$R_1$ is lower alkyl or alkoxy radical or halogen;
$R_2$ is halogen; lower alkyl or alkoxy radical; or
$R_1$ and $R_2$ can together also form an alkylene bridge containing 3 to 5 carbon atoms, which can optionally contain one or more double bonds; and, but less preferably, when $R_1$ is a lower alkyl or alkoxy radical, $R_2$ can also be a hydrogen atom, and physiologically compatible salts and esters thereof, are outstandingly effective as blood sugar-lowering agents.

10 Claims, No Drawings

INDOLE-CARBOXYLIC CARBON COMPOUNDS AND PHARMACEUTICAL COMPOSITIONS CONTAINING THEM

This is a continuation of application Ser. No. 322,818 filed Jan. 11, 1973, now abandoned.

The present invention is concerned with certain novel indole-carboxylic acid compounds, with pharmaceutical compositions containing, and methods using, said indole-carboxylic acid compounds.

It is known that indole-2-carboxylic acid and some mono-substituted indole-2-carboxylic acids exhibit a blood sugar-lowering action on rats and alloxan-diabetic mice (see Bauman et. al., Biochemical Pharmacology, 18, 1241–1243/1969). 5-Methoxyindole-2-carboxylic acid (MICA), in particular, has, because of its marked action, been further investigated by several groups of workers. U.S. Pat. No. 3,332,846 to Gordon discloses experimental data for some mono-substituted indole-2-carboxylic acids, viz., the 5-methoxy material and the 5-methyl material. On the other hand, it is stated in the above-mentioned literature reference that very similar compounds which differ only by the position of the substituents or by the replacement of one group for another, can be ineffective.

We have now found that a group of previously unknown 4,5-disubstituted indole-2-carboxylic acids, as well as a group of 4-mono-substituted indole-2-carboxylic acids, some of which are known, show, surprisingly, a greater blood sugar-lowering action than 5-methoxy-indole-2-carboxylic acid.

Thus, according to one aspect of the present invention, there are provided novel indole-carboxylic acid compounds of the general formula, as well as therapeutic compositions containing them:

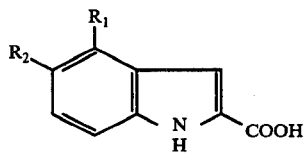
(I), wherein $R_1$ is lower alkyl, alkoxy radical or halogen; and $R_2$ is lower alkyl or alkoxy or halogen; or wherein $R_1$ and $R_2$ together also form an alkylene bridge containing 3 to 5 carbon atoms which can optionally contain one or more double bonds; and, but less preferably, when $R_1$ is a lower alkyl or alkoxy radical, $R_2$ can also be a hydrogen atom; as well as of the physiologically compatible salts and esters thereof, in admixture with a solid liquid pharmaceutical diluent or carrier.

Preferred in the present invention are new indolecarboxylic acids of the formula:

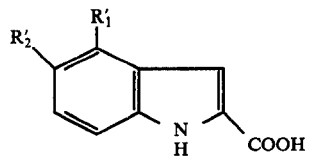
(Ia), wherein $R'_1$ and $R'_2$, which may be the same or different, are lower alkyl or alkoxy radicals or, in the case of $R'_2$, halogen; or $R'_1$ and $R'_2$ can together also form an alkylene bridge containing 3 to 5 carbon atoms, and the physiologically compatible salts and esters thereof.

We have found that certain specific disubstituted materials are substantially more active than the monosubstituted materials for which experimental data has been disclosed in the art referred to hereinabove.

By lower alkyl and alkoxy radicals, there are to be understood those radicals which contain 1 to 5 and preferably 1 to 2 carbon atoms. Furthermore, halogen is to be understood to mean a fluorine, chlorine or bromine atom, the chlorine atom being preferred.

The above-described compounds can be prepared by the processes known from the literature for the preparation of indole-2-carboxylic acids, the preferred processes being the following:

a. treatment, according to Reissert's method, of a compound of the general formula:

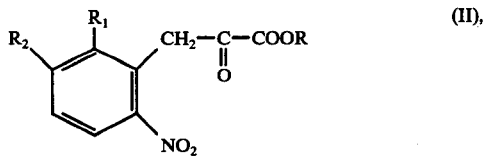
(II), wherein $R_1$ and $R_2$ have the same meanings as above and R is a hydrogen atom or a lower alkyl radical, with a reduction agent, the amino group formed from the nitro group immediately cyclizing with the keto group to form an indole derivative, whereafter, if desired, the ester obtained is saponified to the corresponding free acid; or b. treatment, according to Fischer method, of a compound of the general formula:

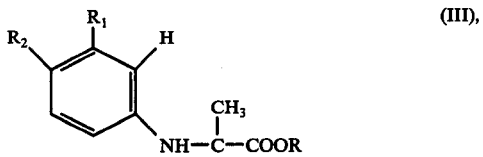
(III), wherein R, $R_1$ and $R_2$ have the same meanings as above, with an acid-reacting condensation agent, an indole derivative being formed by the splitting off of ammonia, whereafter, if desired, the ester obtained is saponified to the corresponding free acid; or c. treatment of an indole derivative of the general formula:

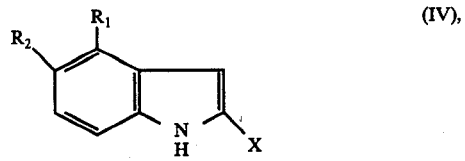
(IV), wherein $R_1$ and $R_2$ have the same meanings as above and X is a radical which is readily oxidized to a carboxyl group, with an appropriate oxidation agent, whereafter, if desired, the carboxylic acid formed is esterified.

If desired, the carboxylic acids obtained by the above-described processes can be converted into their physiologically compatible salts.

The starting materials of general formula (II) can readily be obtained, by ester condensation, from an appropriately substituted o-nitrotoluene and a dialkyl ester of oxalic acid, the potassium alcoholate corresponding to the alkyl radicals in the oxalic acid ester thereby being particularly preferred as condensation agent. By variation of the conditions of working up, the compound of general formula (II) can be isolated either as an ester (R = a lower alkyl radical) or as the free acid (R = a hydrogen atom).

The nitro group of the compounds of general formula (II) can be reduced by a large variety of reducing agents; particularly preferred methods include the use of metals, for example zinc dust, with acids, or the use of metal compounds in lower states of oxidation, for example ferrous salts, in the presence of alkalis, preferably of an aqueous solution of ammonia, as well as other reducing agents, for example sodium dithionite or even hydrogen in the presence of a catalyst.

The starting materials of general formula (III) can be prepared in known manner either from an appropriately substituted phenyl-hydrazinc and pyruvic acid or an ester thereof or also by the Japp-Klingemann method, in which an appropriately substituted aniline is diazotized, wherafter the solution of the diazonium salt obtained is reacted with an alkaline solution of an alkyl 2-methyl-acetoacetate or with a dialkyl 2-oxaloproprionate (see J. Org. Chem., 34, 3002/1969).

The cyclization of the hydrazones of general formula (III) can be carried out with an acid, for example a hydrohalic acid, sulfuric acid, a sulfonic acid or a strongly acidic ion exchanger, in a polar solvent, for example an alcohol, glacial acetic acid or water, but there can also be used polyphosphoric acid or a catalyst, for example boron trifluoride, a metal salt, such as aluminum oxide, at elevated temperatures.

As oxidizable group X in the compounds of general formula (IV), there is preferably used a hydroxymethyl, aminomethyl, formyl or acetyl radical or a functional derivative thereof, which can easily be oxidized to the carboxy group with conventional oxidizing agents, for example, with a permanganate or dichromate, in the case of an acetyl radical, especially with a hypohalite solution (the so-called haloform reaction), and in the case of the formyl radical also with atmospheric oxygen.

As physiologically compatible salts, there may, in particular, be mentioned the alkali metal, alkaline earth metal and ammonium salts, as well as the salts with basic compounds with a blood sugar-lowering action, preferably biguanides, which are also new compounds. These salts can be prepared, for example, by reaction of the free bases or carbonates with the indole-2-carboxylic acids.

The following Examples are given for the purpose of illustrating the present invention:

EXAMPLE 1

Preparation of 4,5-Dimethylindole-2-carboxylic acid.

20 g 2,3,4-trimethylnitrobenzene were reacted in ether, under the conditions of an ester condensation, with 38 g diethyl oxalate and freshly prepared potassium ethylate (prepared from 9.5 g potassium and 36 g ethanol). After standing for two days, the resultant crystal slurry was filtered off with suction, dissolved in water and the solution was extracted with ether. The ether was discarded and the solution acidified. The 3-(2,3-dimethyl-6-nitrophenyl)-pyruvic acid which thereby precipitated out was purified by boiling up with toluene and methylene chloride, whereafter it melted at 144°–146° C. The yield was 20 g (73% of theory). This acid was sufficiently pure for further working up. However, after recrystallization from toluene, it has a melting point of 151°–153° C.

19.3 g 3-(2,3-dimethyl-6-nitrophenyl)-pyruvic acid were dissolved in 400 ml ethanol and hydrogenated in the presence of palladium/charcoal at ambient temperature and atmospheric pressure. After termination of the take-up of hydrogen (6.1 liters), the catalyst was filtered off, the filtrate was evaporated to dryness and the residue was mixed with an aqueous solution of potassium hydroxide to form the corresponding potassium salt which was then recrystallized from a little water. Thereafter, the salt was dissolved in a large volume of water and the solution was acidified with hydrochloric acid. There was thus obtained pure 4,5-dimethylindole-2-carboxylic acid in a yield of 57% of theory; m.p. 248° C (decomp.).

The following compounds were obtained in an analogous manner:

4-methoxy-5-methylindole-2-carboxylic acid m.p. 222°–224° C. (decomp.) (recrystallized from ethyl acetate)

The compound was prepared via 2,6-dimethyl-3-nitroanisole (b.p. 94°–98° C/0.4 mm Hg) and 3-(2-methoxy-3-methyl-6-nitrophenyl)-pyruvic acid (m.p. 140°–142° C).

4,5-dimethoxyindole-2-carboxylic acid m.p. 245°–247° C. (decomp.) (recrystallized from ethanol/water)

The compound was prepared via 3-(2,3-dimethoxy-6-nitrophenyl)-pyruvic acid (m.p. 131°–133° C).

4-ethyl-5-methylindole-2-carboxylic acid m.p. 244°–246° C. (decomp.) (recrystallized from ethanol/water)

The compound was prepared via 3-ethyl-2,4-dimethylnitrobenzene (b.p. 141°–145° C/11mm Hg) and 3-(2-ethyl-3-methyl-6-nitrophenyl)-pyruvic acid (m.p. 135° C (decomp.).

4-butoxy-5-methylindole-2-carboxylic acid m.p. 149°–150° C.

The compound was prepared via 3-butoxy-2,4-dimethylnitrobenzene (b.p. 129°–131° C/0.4 mm Hg) and 3-(2-butoxy-3-methyl-6-nitrophenyl)-pyruvic acid (m.p. 90°–91° C).

EXAMPLE 2

Preparation of 4,5-Dimethylindole-2-carboxylic acid and the ethyl ester thereof 20 g 2,3,4-trimethylnitrobenzene were reacted in ether, under the conditions of an ester condensation, with 19.8 g diethyl oxalate and freshly prepared potassium ethylate (prepared from 7.4 g potassium and 28 g ethanol). After standing for two days, the resultant crystal slurry was dissolved in absolute ethanol and the solution was neutralized with glacial acetic acid. Subsequently it was evaporated, the residue was taken up in water, the oily ester was extracted with ether and the ethereal solution was dried and then evaporated. The 18 g of ester obtained were, without further purification, dissolved in 100 ml ethanol and hydrogenated in the presence of palladium/charcoal, at ambient temperature and atmospheric pressure. The take-up of hydrogen was 4.9 liters. After termination of the hydrogen take-up, the catalyst was filtered off and the solution evaporated until it crystallized. The ethyl 4,5-dimethylindole-2-carboxylate thus obtained melted at 143°–145° C. The yield was 9.0 g (61% of theory).

After saponification of 19 g of this ethyl ester with 15 g potassium hydroxide in 120 ml methanol, recrystallization of the potassium salt from a little water and acidification of the dilute aqueous solution with hydrochloric acid, there were obtained 14.0 g (85% of theory) 4,5-dimethylindole-2-carboxylic acid; m.p. 250° C.

The following compounds were obtained in an analogous manner:

5-methoxy-4-methylindole-2-carboxylic acid and its ethyl ester ethyl ester: m.p. 158° C (recrystallized from toluene) acid: m.p. 233° C (decomp.) (recrystallized from 2-nitropropane)

The preparation took place via ethyl 3-(3-methoxy-2-methyl-6-nitrophenyl)-pyruvate (m.p. 80° C).

4-methoxy-5-methylindole-2-carboxylic acid and its ethyl ester ethyl ester: m.p. 117°-120° C (recrystallized from ethanol) acid: m.p. 222°-224° C (decomp.) (recrystallized from ethyl acetate)

The preparation took place via ethyl 3-(2-methoxy-3-methyl-6-nitrophenyl)-pyruvate (oil).

EXAMPLE 3

Preparation of 4-Chloro-5-methylindole-2-carboxylic acid

In a manner analogous to that described in Example 1, from 78.1 g 3-chloro-2,4-dimethylnitrobenzene (b.p. 115° C/6 mm Hg; prepared from 2,6 dimethyl-3-nitroaniline by the Sandmeyer reaction in 85% yield), there was prepared, by ester condensation in ether with 170.5 ml diethyl oxalate and potassium ethylate (prepared from 31.8 g potassium and 143 ml ethanol), 3-(2-chloro-3-methyl-6-nitrophenyl)-pyruvic acid, which has a melting point of 120°-122° C. The yield was 39.7 g (36.6% of theory).

35.0 g of this pyruvic acid derivative were dissolved in 470 ml water and 63 ml 2N aqueous sodium hydroxide solution and, while stirring vigorously, about 60 g sodium dithionite were introduced in small amounts until the reaction solution no longer showed a temperature increase. The reaction was finished when, after the addition of further aqueous sodium hydroxide solution, there was neither red coloration nor a further temperature increase after the addition of further dithionite. After acidification with concentrated hydrochloric acid, 4-chloro-5-methylindole-2-carboxylic acid precipitated out. After filtering off with suction, it was again converted into the sodium salt, which can be recrystallized from a little water. Finally, the free acid was again precipitated out and, thereafter, recrystallized from ethyl acetate. It had a boiling point of 279°-281° C (decomp,. The yield was 17.4 g (61% of theory).

The following compounds are obtained in analogous manner:

5-Bromo-4-methylindole-2-carboxylic acid

The compound was prepared via 3-(3-bromo-2methyl-6-nitrophenyl)-pyruvic acid.

4-Chloro-5-methoxyindole-2-carboxylic acid m.p. 273°-274° C. (decomp.) (recrystallized from methanol/water The compound was prepared via 3-(2-chloro-3-methoxy-6-nitrophenyl)-pyruvic acid (m.p. 210°-215° C)

5-Chloro-4-methoxyindole-2-carboxylic acid m.p. 253°-255° C. (decomp.) (recrystallized from ethyl acetate)

The compound was prepared via 3-(3-chloro-2-methoxy-6-nitrophenyl)pyruvic acid (m.p. 85°-87° C)

5-Chloro-4-methylindole-2-carboxylic acid m.p. 256° C. (recrystallized from ethyl acetate/benzene)

The compound was prepared via 4-chloro-2,3-dimethylnitrobenzene (m.p. 57°-58° C) and 3-(3-chloro-2-methyl-6-nitrophenyl)-pyruvic acid (oil).

5-Fluoro-4-methylindole-2-carboxylic acid m.p. 220°-222° C. (decomp.) (recrystallized from ethanol/water.

The compound was prepared via 3-(3-fluoro-2-methyl-6-nitrophenyl)pyruvic acid (m.p. 126°-128° C).

4-Bromo-5-methylindole-2-carboxylic acid m.p. 278°-279° C. (recrystallized from ethyl acetate)

The compound was prepared via 3-bromo-2,4-dimethylnitrobenzene (m.p. 52° C) and 3-(2-bromo-3-methyl-6-nitrophenyl)pyruvic acid (m.p. 196° C).

EXAMPLE 4

Preparation of 4,5-Tetramethyleneindole-2-carboxylic acid and its ethyl ester.

6.4 g 6-amino-1,2,3,4-tetrahydronaphthalene hydrochloride were diazotized in hydrochloric acid solution with 2.65 g sodium nitrite and the diazonium salt solution thus obtained was added portionwise to a solution of 5.0 g ethyl 2-methylacetoacetate in aqueous potassium hydroxide solution (8.5 g potassium hydroxide in 21 ml water). Thereafter, it was acidified with a mixture of 21 ml concentrated hydrochloric acid and 100 g ice and the hydrazone which precipitated out was taken up in ether. The etheral solution was dried over anhydrous sodium sulfate and the ether evaporated in a vacuum. The hydrazone did not crystalize. It was dissolved in 90 ml ethanol and hydrogen chloride passed in, with ice cooling, until the solution was saturated. While passing in further hydrogen chloride, it was heated under reflux for 7 minutes, cooled and poured on to ice. The product was extracted with ether and the ethereal solution was dried and evaporated and the residue brought to crystallization with toluene or cyclohexane. The ethyl 4,5-tetramethyleneindole-2-carboxylate thus obtained melted at 130°-132° C; the yield was 4.5 g (53% of theory).

For saponification, 4,5 g of this ethyl ester were heated under reflux for 1.5 hours with 3.8 g potassium hydroxide in 50 ml methanol, the potassium salt of 4,5-tetramethyleneindole-2-carboxylic acid thereby precipitating out. It can be recrystallized from a little water. A solution of the potassium salt in water was mixed with hydrochloric acid to precipitate out the free 4,5-tetramethyleneindole-2-carboxylic acid. It can be recrystallized from ethanol. It has a melting point of 236° C (decomp.). The yield was 3.2 g (80% of theory).

The following compound was obtained in an analogous manner:

4,5-Dichloroindole-2-carboxylic acid m.p. 249°-253° C (decomp.). (recrystallized from ethyl acetate)

The compound was prepared via 3,4-dichlorophenylhydrazine and ethyl pyruvate (3,4-dichlorophenyl)- hydrazone (m.p. 108°–111° C) by ring closure with polyphosphoric acid and saponification of the resultant ester.

EXAMPLE 5

Preparation of 4,5-Dimethylindole-2-carboxylic acid

In a manner analogous to that described in Example 4, 60.6 g 3,4-dimethylaniline were diazotized with 37.0 g sodium nitrite and reacted with 73.0 g ethyl 2-methyl-acetoacetate to give ethyl pyruvate (3,4-dimethyl-phenylhydrazone), which does not crystallize. A greater part of the dark brown impurities present can be removed by treatment of a solution of the hydrazone in ligroin with silica gel. After evaporation of the ligroin, the hydrazone (81.1 g; 49% of theory) was dissolved in ethanol and hydrogen chloride was passed in, with ice cooling, until the solution was saturated. While passing in further hydrogen chloride, the solution was heated under reflux for 15 minutes, whereafter the reaction mixture was cooled and filtered with suction. The filtrate was evaporated to dryness and the residue digested several times with warm ligroin. The ligroin was evaporated somewhat and cooled. The ester which thereby crystallized out (31.6 g; 42% of theory) was filtered off with suction and, for saponification, heated under reflux for one hour with 27 g potassium hydroxide in 230 ml methanol. Thereafter, the reaction mixture was cooled and filtered with suction. The filtrate was treated with active charcoal and thereafter evaporated to dryness. The residue was taken up in water, again clarified with active charcoal and acidified with hydrochloric acid. The product was filtered off with suction and recrystallized twice from isopropanol; the 4,5-dimethylindole-2-carboxylic acid obtained (3.6 g; 13% of theory) then has a melting point of 247°–250° C (decomp.).

The following compound was obtained in an analogous manner:

4,5-trimethyleneindole-2-carboxylic acid m.p. 230°–233° C. (decomp.) (recrystallised from ethanol/water)

The compound was prepared via ethyl 4,5-trimethyleneindole-2-carboxylate (m.p. 169°–170° C.).

EXAMPLE 6

1-Phenethyl-biguanide salt of 3H-benzo [e]indole-2-carboxylic acid

3H-Benzo[e]indole-2-carboxylic acid was dissolved in the calculated amount of 2N aqueous sodium hydroxide solution and, by stirring in solid sodium chloride, the sodium salt of 3H-benzo[e]indole-2-carboxylic acid was precipitated out. It was filtered off with suction, washed with a little water and dried.

11.7 g. of this sodium salt and 11.4 g. 1-phenethyl-biguanide hydrochloride were heated under reflux for 3 hours in 500 ml. ethanol. The sodium chloride formed was filtered off with suction, the filtrate was evaporated and the residue was recrystallised from water. The compound crystallised with 1 mole water of crystallisation. The yield was 17.2 g. (80% of theory) 1-phenethyl-biguanide salt of 3H-benzo[e]indole-carboxylic acid; m.p. 149°–152° C.

3H-benzo[e]indole-2-carboxylic acid can be prepared, for example, by the method described by Goldsmith et al. (J. Org. Chem., 18, 507/1953).

The following compounds were obtained in an analogous manner:

1-butyl-biguanide salt of 3H-benzo[e]indole-2-carboxylic acid m.p. 145°–148° C. (recrystallised from water).

1-phenethyl-biguanide salt of 4,5-dimethylindole-2-carboxylic acid m.p. 147°–149° C. (recrystallised from water).

The following Examples illustrate several pharmaceutical compositions according to the present invention:

EXAMPLE 7

Tablets

For each tablet, 200 mg. finely ground 4-methylindole-2-carboxylic acid, 50 mg. powdered lactose and 65.5 g. maize starch were seived and mixed. A 15% slurry was prepared from 10 mg. maize starch. The above mixture was granulated in a kneader with this slurry. The moist granulate was passed through a 1.9 mm. sieve and then dried. The dried granulate was passed through a 1.4 mm. sieve and then mixed with 10 mg. sodium carboxymethylamylopectin, 12 mg. talc and 2.5 mg. magnesium stearate. The finished mass was pressed into scored, oblong tablets. They have a weight of 350 mg., a diameter of 6 mm. and a length of 13 mm.

4-Methylindole-2-carboxylic acid can be prepared, for example, by the method described by Andrisano et al., (Gazz. chim. ital., 87, 949/1957).

EXAMPLE 8

Gelatine capsules 167.5 mg. sodium 4,5-dimethylindole-2-carboxylate (corresponding to 150 mg. of the free carboxylic acid) were placed into special gelatine capsules obtained from the firm Scherer, the capsules having the following composition:

about 70% gelatine USP
about 15% glycerol
about 10% sorbitol
about 1.5% mannitol
about 3% oligosaccharides
about 0.7% titanium dioxide
about 0.2–3% permitted foodstuff colours

EXAMPLE 9

Syrup

| | |
|---|---|
| sodium 4-methoxyindole-2-carboxylate | 4.46 g. |
| starch syrup | 65.00 g. |
| kaolin | 5.00 g. |
| saccharine sodium | 0.30 g. |
| sweet orange essence | 0.10 ml. |
| butyl p-hydrobenzoate | 0.03 g. |
| distilled water | ad 100.00 ml. |

One teaspoon (5 ml.) of this syrup contains 200 mg. 4-methoxyindole-2-carboxylic acid.

4-Methoxyindole-2-carboxylic acid can be prepared, for example, by the method described by Pappalardo et al. (Gazz. chim. ital., 88, 574/1958).

EXAMPLE 10

Ampoules

For each ampoule, 165.6 mg. sodium 3H-benzo[e]-indole-2-carboxylate (corresponding to 150 mg. of the free carboxylic acid) and 4.5 mg. sodium chloride were dissolved in bidistilled water, made up to 5 ml., filtered through a membrane filter (Schleicher & Schull No. 1121), filled into white ampoules and sterilised for 20 minutes at 121° C.

The blood sugar-lowering compositions according to the present invention include all the conventional forms for oral and parenteral administration, for example, tablets, capsules, dragees, syrups, solutions, suspensions, drops, suppositories and the like. For this purpose, the active materials are mixed with solid or liquid pharmaceutical diluents or carriers and subsequently brought into the desired form. Examples of solid carrier materials include starch, lactose, mannitol, methylcellulose, talc, highly dispersed silicic acid, high molecular weight fatty acids (for example stearic acid), gelatine, agaragar, calcium phosphate, magnesium stearate, animal and vegetable fats and solid high molecular weight polymers (for example polyethylene glycols). Compositions suitable for oral administration can, if desired, also contain flavoring and/or sweetening agents. As injection medium, it is preferred to use water which contains the conventional additives for injection solutions, for example stabilizing agents, solubilizing agents and/or buffers. Compositions intended for injection must, of course, be sterile. Additives for injection solutions include, for example, acetate and tartrate buffers, ethanol, complex-forming agents (for example ethylene-diaminetetraacetic acid and the non-toxic salts thereof) and high molecular weight polymers (for example liquid polyethylene oxide) for viscosity regulation.

The blood sugar-lowering effectiveness of the indolecarboxylic acids according to the present invention was tested on various experimental animals and compared with MICA.

EXPERIMENT A

The test compounds were administered intraperitoneally, as a solution of the sodium salt, to fasting male Sprague-Dawley rats with a body weight of 200–220 g. In the following Table 1, there is given the threshold dose which significantly lowers the blood sugar level. From this is calculated the relative effectiveness, referred to MICA as 1.

TABLE 1

| test compound | threshold dose | relative action |
|---|---|---|
| MICA (5-methoxyindole-2-carboxylic acid) | 25 mg/kg | 1 |
| 3H-benzo[c]indole-2-carboxylic acid | 20 mg/kg | 1.25 |
| 4-methylindole-2-carboxylic acid | 5 mg/kg | 5 |
| 4-methozyindole-2-carboxylic acid | 10 mg/kg | 2.5 |
| 4,5-dimethylindole-2-carboxylic acid | 5 mg/kg | 5 |
| 5-methoxy-4-methylindole-2-carboxylic acid | 10-20 mg/kg | about 2 |
| 4,5-trimethyleneindole-2-carboxylic acid | 20 mg/kg | 1.25 |
| 4-ethyl-5-methylindole-2-carboxylic acid | 20 mg/kg | 1.25 |
| 4-methoxy-5-methylindole-2-carboxylic acid | 20 mg/kg | 1.25 |
| 4-chloro-5-methylindole-2-carboxylic acid | 20 mg/kg | 1.25 |
| 5-chloro-4-methylindole-2-carboxylic acid | 5 mg/kg | 5 |
| 5-chloro-4-methoxyindole-2-carboxylic acid | 20 mg/kg | 1.25 |
| 5-fluoro-4-methylindole-2-carboxylic acid | 10 mg/kg | 2.5 |

EXPERIMENT B

The test compounds were administered intravenously, as a solution of the sodium salt, to fasting rabbits of both sexes with an approximate body weight of 2 kg. In the following Table 2, there is given the threshold dose which significantly lowers the blood sugar level. From this is calculated the relative effectiveness, referred to MICA as 1.

TABLE 2

| test compound | threshold dose | relative action |
|---|---|---|
| MICA(5-methoxyindole-2-carboxylic acid) | 50 mg/kg | 1 |
| 3H-benzo[o]indole-2-carboxylic acid | 25 mg/kg | 2 |
| 4-methylindole-2-carboxylic acid | 20 mg/kg | 2.5 |
| 4-methoxyindole-2-carboxylic acid | 10 mg/kg | 5 |
| 4,5-dimethylindole-2-carboxylic acid | 20-25 mg/kg | 2-2.5 |
| 5-methoxy-4-methylindole-2-carboxylic acid | 20 mg/kg | 2.5 |
| 4,5-trimethylindole-2-carboxylic acid | 40 mg/kg | 1.25 |
| 4-chloro-5-methylindole-2-carboxylic acid | 30 mg/kg | 1.7 |
| 4-chloro-5-methoxyindole-2-carboxylic acid | 40 mg/kg | 1.25 |
| 5-chloro-4-methylindole-2-carboxylic acid | 20 mg/kg | 2.5 |

EXPERIMENT C

The test compounds were administered intraperitoneally, as a solution of the sodium salt, to fasting male guinea pigs with body weights of up to 400 g. The following Table 5 gives the threshold doese which sinificantly lowers the blood sugar level. From this is calculated the relative action, referred to MICA as 1.

TABLE 3

| test substance | threshold dose | relative action |
|---|---|---|
| MICA (5-methoxyindole-2-carboxylic acid) | 75 mg/kg | 1 |
| 3H-benzo[o]indole-2-carboxylic acid | 40 mg/kg | about 2 |
| 4-methylindole-2-carboxylic acid | 30 mg/kg | 2.5 |
| 4-methoxyindole-2-carboxylic acid | 60 mg/kg | about 1.2 |
| 4,5-dimethylindole-2-carboxylic acid | 30 mg/kg | 2.5 |
| 4,5-trimethyleneindole-2-carboxylic acid | 40 mg/kg | about 2 |
| 4,5-tetramethyleneindole-2-carboxylic acid | 40 mg/kg | about 2 |
| 5-methoxy-4-methylindole-2-carboxylic acid | 30 mg/kg | 2.5 |
| 4-chloro-5-methylindole-2-carboxylic acid | 30 mg/kg | 2.5 |
| 4-chloro-5-methoxyindole-2-carboxylic acid | 20 mg/kg | about 4 |
| 5-chloro-4-methylindole-2-carboxylic acid | 50 mg/kg | 1.5 |

EXPERIMENT D

Female Alloxan-diabetic mice with a weight of at least 20 g and with an average fasting blood sugar level of 500 mg.% were injected intraperitoneally with the test substances, in the form of the sodium salt, at a dosage level of 25 mg/kg. The blood sugar level was determined 0.2 and four hours after administration of the test substance, for which purpose 0.1 ml of blood was taken and the glucose content thereof determined by the hexokinase method, using the haemolysate technique.

The results obtained are summarized in the following Table 4, each value given being the average value from 10 to 20 animals. The results obtained show that the compound according to the present invention possesses a significantly greater and longer lasting action than the known comparison substance MICA.

TABLE 4

| | Blood sugar value in mg.% and % of the control | | | | | |
|---|---|---|---|---|---|---|
| | 0 | | 2 | | 4 | |
| time in hours | mg.% | % of control | mg.% | % of control | mg.% | % of control |
| 5-methoxyindole-2-carboxylic acid | 500 | 100 | 310 | 76 | 315 | 97 |
| 4,5-dimethylindole- | 500 | 100 | 165 | 40 | 260 | 80 |

TABLE 4-continued

| | Blood sugar value in mg.% and % of the control | | | | | |
|---|---|---|---|---|---|---|
| | 0 | | 2 | | 4 | |
| time in hours | mg. % | % of control | mg. % | % of control | mg. % | % of control |
| 2-carboxylic acid control | 500 | — | 410 | — | 325 | — |

While the method of administering the active ingredients of the novel compositions of matter of the present invention is not limited to oral administration, a decided advantage of the present invention is that the active ingredients may be administered orally in any convenient manner. They may be taken orally, for example, with an inert diluent or with an assimilable edible carrier, or they may be compressed into tablets, or enclosed in hard or soft gelatin capsules. Furthermore, the active ingredients may be administered either individually or as mixtures of a plurality of such active ingredients. The amount of a single dose or of a daily dose necessary to induce a particular level of hypoglycemia will vary with the size or weight of the warmblooded animal to be treated.

Generally, it should be such as to give a proportionate dosage of from about 2.5 mg to about 25 mg per kg of body weight per day of, for example, 5-methoxyindole-2-carboxylic acid, a highly active compound, or other active ingredient or mixture thereof. In terms of total weight of active ingredient, the daily dosage for warm-blooded animals of, for example, 75 kilograms, would amount to from about 0.1 g to about 2.0 g. The dosage regimen may be adjusted to provide optimum therapeutic response; for example, several divided doses may be administered daily or the dose may be proportionately reduced or increased as the requirements of the therapeutic situation would indicate.

It will be understood that the specification and examples are illustrative but not limitative of the present invention and that other embodiments within the spirit and scope of the invention will suggest themselves to those skilled in the art.

What is claimed is:

1. A compound selected from
   4-methoxy-5-methylindole-2-carboxylic acid,
   5-methoxy-4-methylindole-2-carboxylic acid, and the pharmaceutically acceptable salts and lower alkyl esters thereof.
2. 4-Methoxy-5-methylindole-2-carboxylic acid.
3. 5-Methoxy-4-methyl-indol-2-carboxylic acid.
4. Ethyl-5-methoxy-4-methyl-indol-2-carboxylate.
5. Method of depressing the blood sugar level in a subject which method comprises administrating to said subject an anti-diabetically effective amount of a compound selected from
   4-methoxy-5-methylindole-2-carboxylic acid,
   5-methoxy-4-methylindole-2-carboxylic acid, and the pharmaceutically acceptable salts and lower alkyl esters thereof.
6. Method as claimed in claim 5 wherein the compound is 4-methoxy-5-methylindole-2-carboxylic acid.
7. Method as claimed in claim 5 wherein the compound is 5-methoxy-4-methylindole-2-carboxylic acid.
8. Method as claimed in claim 5 wherein the compound is ethyl 5-methoxy-4-methylindole-2-carboxylate.
9. Therapeutic composition having anti-diabetic properties comprising pharmaceutically acceptable carriers and, in anti-diabetically effective amount, a compound as claimed in claim 1.
10. A composition as claimed in claim 9 in dosage unit form wherein a dosage unit contains from 0.1 to 2.0 grams of active ingredient.

* * * * *